(12) United States Patent
Hwang et al.

(10) Patent No.: US 11,904,291 B2
(45) Date of Patent: Feb. 20, 2024

(54) APPARATUS FOR PREPARING OLIGOMER

(71) Applicant: LG CHEM, LTD., Seoul (KR)

(72) Inventors: Moon Sub Hwang, Daejeon (KR); Min Ho Sun, Daejeon (KR); Jong Hun Song, Daejeon (KR); Kyung Seog Youk, Daejeon (KR); Jeong Seok Lee, Daejeon (KR); Hong Min Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 94 days.

(21) Appl. No.: 17/629,359

(22) PCT Filed: Jul. 9, 2021

(86) PCT No.: PCT/KR2021/008786
§ 371 (c)(1),
(2) Date: Jan. 21, 2022

(87) PCT Pub. No.: WO2022/065645
PCT Pub. Date: Mar. 31, 2022

(65) Prior Publication Data
US 2022/0347648 A1 Nov. 3, 2022

(30) Foreign Application Priority Data

Sep. 22, 2020 (KR) ........................ 10-2020-0121969

(51) Int. Cl.
*B01J 19/26* (2006.01)
*B01J 4/00* (2006.01)
(Continued)

(52) U.S. Cl.
CPC ............... *B01J 19/26* (2013.01); *B01J 4/002* (2013.01); *B01J 10/00* (2013.01); *C07C 2/08* (2013.01); *B01J 2204/002* (2013.01)

(58) Field of Classification Search
CPC ... B01J 19/26; B01J 4/002; B01J 10/00; B01J 2204/002; B01J 2219/00247;
(Continued)

(56) References Cited

U.S. PATENT DOCUMENTS 6,117,399 A   9/2000  Jorgensen et al.
8,829,232 B2  9/2014  Penzel et al.
(Continued)

FOREIGN PATENT DOCUMENTS

CN   1033754 A   7/1989
CN   1124029 A   6/1996
(Continued)

*Primary Examiner* — Ali Z Fadhel
(74) *Attorney, Agent, or Firm* — Bryan Cave Leighton Paisner LLP

(57) ABSTRACT

The present disclosure relates to an apparatus for preparing an oligomer, and more particularly, to an apparatus for preparing an oligomer including: a reactor including a gaseous area having a first gaseous reactant inlet provided at a lower portion thereof, and a reaction area in which a reaction medium reacts with the gaseous reactant above the gaseous area; a second gaseous reactant inlet provided on an inner wall of the reactor in the gaseous area and a third gaseous reactant inlet provided on an inner wall of the reactor facing the second gaseous reactant inlet; and a first injection nozzle connected to the second gaseous reactant inlet and a second injection nozzle connected to the third gaseous reactant inlet.

11 Claims, 2 Drawing Sheets

(51) Int. Cl.
*B01J 10/00* (2006.01)
*C07C 2/08* (2006.01)

(58) Field of Classification Search
CPC ............ B01J 2219/00252; B01J 10/002; B01J 19/002; B01J 19/006; B01J 19/0006; C07C 2/08; C07C 2531/14; C07C 2531/22; C07C 2/32; C07C 7/10; C07C 7/148; C07C 11/107
See application file for complete search history.

(56) References Cited

U.S. PATENT DOCUMENTS

| | | | |
|---|---|---|---|
| 2005/0020866 A1* | 1/2005 | Kobayashi | C08F 10/00 585/502 |
| 2007/0217966 A1 | 9/2007 | Heino et al. | |
| 2009/0214405 A1* | 8/2009 | Schneider | C07C 7/00 422/231 |
| 2014/0058161 A1 | 2/2014 | Bedard et al. | |
| 2016/0200643 A1 | 7/2016 | Nyce et al. | |
| 2018/0030181 A1* | 2/2018 | Emoto | C08F 10/02 |

FOREIGN PATENT DOCUMENTS

| | | |
|---|---|---|
| CN | 1214958 A | 4/1999 |
| CN | 1261377 A | 7/2000 |
| CN | 1917951 A | 2/2007 |
| CN | 101291727 A | 10/2008 |
| CN | 104209069 A | 12/2014 |
| CN | 205329209 U | 6/2016 |
| CN | 105833805 A | 8/2016 |
| CN | 107438479 A | 12/2017 |
| CN | 107782145 A | 3/2018 |
| CN | 110603092 A | 12/2019 |
| DE | 102012014393 A1 | 1/2014 |
| EP | 1777000 A1 | 4/2007 |
| EP | 2397221 A1 | 12/2011 |
| JP | 08-024836 B2 | 3/1996 |
| JP | 2009511267 A | 3/2009 |
| JP | 2017066130 A | 4/2017 |
| KR | 10-2004-0099973 A | 12/2004 |
| KR | 10-0509286 B1 | 8/2005 |
| KR | 10-2007-0057851 A | 6/2007 |
| KR | 10-0928061 B1 | 11/2009 |
| KR | 10-2011-0106856 A | 9/2011 |
| KR | 10-1065747 B1 | 9/2011 |
| KR | 10-1183319 B1 | 9/2012 |
| KR | 10-2013-0069745 A | 6/2013 |
| KR | 10-1418910 B1 | 7/2014 |
| KR | 10-1535058 B1 | 7/2015 |
| KR | 10-1596578 B1 | 2/2016 |
| KR | 10-2018-0062972 A | 6/2018 |
| KR | 10-2095665 B1 | 3/2020 |
| WO | 2018210780 A1 | 11/2018 |

* cited by examiner

[FIG. 1]
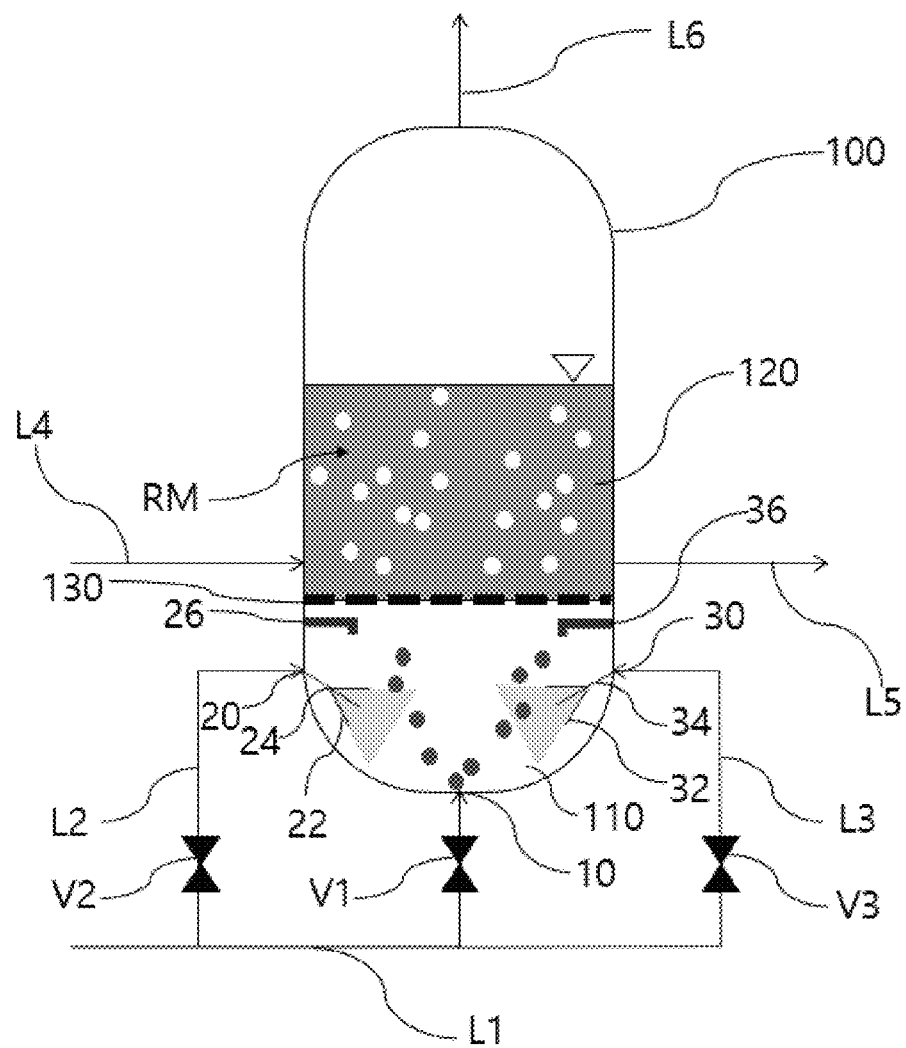

[FIG. 2]
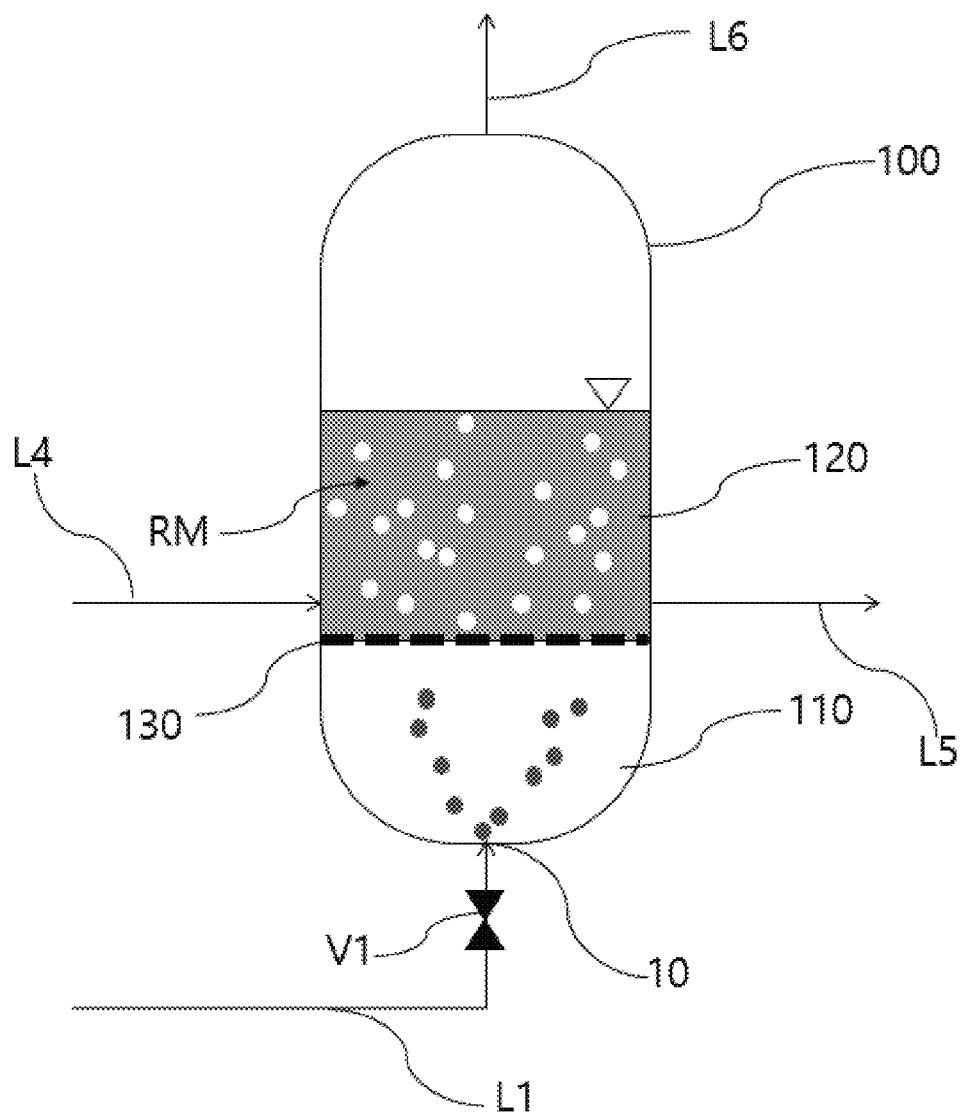

APPARATUS FOR PREPARING OLIGOMER

CROSS-REFERENCE TO RELATED APPLICATIONS

The present application is a National Phase entry pursuant to 35 U.S.C. § 371 of International Application No. PCT/KR2021/008786, filed on Jul. 9, 2021, and claims the benefit of and priority to Korean Patent Application No. 10-2020-0121969, filed on Sep. 22, 2020, the entire contents of which are incorporated by reference in their entirety for all purposes as if fully set forth herein.

TECHNICAL FIELD

The present invention relates to an apparatus for preparing an oligomer, and more particularly, to an apparatus for preparing an oligomer for ensuring a stable operation time without stopping a process operation by minimizing process instability in a short time when a weeping phenomenon occurs inside a reactor.

BACKGROUND ART

An α-olefin (alpha-olefin) is an important material which is used in comonomers, detergents, lubricants, plasticizers, etc., and is commercially widely used. Among them, 1-hexene and 1-octene have been widely used as comonomers for adjusting the density of polyethylene in the preparation of linear low density polyethylene (LLDPE).

The α-olefins have been prepared representatively by an oligomerization reaction of ethylene. As a type of a reactor in which the oligomerization reaction of ethylene is performed, a bubble column reactor for performing the oligomerization reaction (a trimerization reaction or a tetramerization reaction) of ethylene by bringing gaseous ethylene used as a reactant into contact with a reaction area including a liquid reaction medium containing a catalyst has been used.

In the bubble column reactor, a gaseous reactant is introduced into and at the same time, dispersed in the reaction area including the liquid reaction medium through a porous dispersion plate installed at a lower portion of the bubble column reactor, and turbulence is generated by a force of the dispersed gas, such that the liquid reaction medium and the gaseous reactant are naturally mixed with each other.

In this case, the most ideal position of a gaseous reactant inlet for efficient mixing is at the center of a lower portion of the reactor. However, in an initial stabilization stage in which the mixing is performed, problems such as a hindrance of the dispersed flow of the gaseous reactant due to polymers, which are by-products generated during a catalytic reaction, other than a desired oligomer according to the reaction, or a momentary decrease in a supply flow rate of the gaseous reactant due to an operator's mistake in operating a flow rate control device may occur.

As a result, weeping, which is a phenomenon in which a part of the liquid reaction medium in the reaction area is dropped into the gaseous area at a lower portion of the reactor, may occur, and in this case, the liquid reaction medium falling into the gaseous area may block the gaseous reactant inlet, thereby continuously obstructing the injection and flow of gas. Accordingly, a mixing efficiency in the reaction area is significantly reduced, resulting in a problem of shutting down the operation of an entire process.

Thus, in order to solve the above problems, there is a need for measures for ensuring a stable operation time without stopping a process operation by minimizing process instability in a short time when a weeping phenomenon occurs inside a reactor.

DISCLOSURE

Technical Problem

An object of the present invention is to provide an apparatus for preparing an oligomer for ensuring a stable operation time without stopping a process operation by minimizing process instability in a short time when a weeping phenomenon occurs inside a reactor.

Technical Solution

In one general aspect, an apparatus for preparing an oligomer includes: a reactor including a gaseous area having a first gaseous reactant inlet provided at a lower portion thereof, and a reaction area including a reaction medium in contact with the gaseous reactant above the gaseous area; a second gaseous reactant inlet provided on an inner wall of the reactor in the gaseous area and a third gaseous reactant inlet provided on an inner wall of the reactor facing the second gaseous reactant inlet; and a first injection nozzle connected to the second gaseous reactant inlet and a second injection nozzle connected to the third gaseous reactant inlet.

In another general aspect, a method for preparing an oligomer using the apparatus for preparing an oligomer described above includes: supplying a gaseous reactant to the gaseous area through the second and third gaseous reactant supply lines by closing the first flow rate control device and opening second and third flow rate control devices when the first gaseous reactant inlet is blocked.

Advantageous Effects

An apparatus for preparing an oligomer according to the present invention may ensure a stable operation time without stopping a process operation by minimizing process instability in a short time when a weeping phenomenon occurs inside the reactor.

DESCRIPTION OF DRAWINGS

FIG. 1 is a schematic diagram illustrating an apparatus for preparing an oligomer according to an exemplary embodiment of the present invention.

FIG. 2 is a schematic diagram illustrating the configuration of a conventional bubble column reactor for preparing an oligomer.

DETAILED DESCRIPTION

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

The term "stream" in the present invention may refer to a fluid flow in the process, or may refer to the fluid itself flowing in a moving line (pipe). Specifically, the "stream" may refer to both a fluid itself flowing in a pipe connecting each device and a fluid flow. In addition, the fluid may mean that any one or more of gas, liquid, and solid are included.

The term "C#" in the present invention in which "#" is a positive integer refers to all hydrocarbons having #carbon atoms. Thus, the term "C10" refers to a hydrocarbon compound having 10 carbon atoms. In addition, the term "C#+" refers to all hydrocarbon molecules having # or more carbon atoms. Thus, the term "C10+" refers to a mixture of hydrocarbons having 10 or more carbon atoms.

Hereinafter, in order to assist in understanding the present invention, the present invention will be described in more detail with reference to FIGS. 1 and 2 below.

According to an exemplary embodiment of the present invention, there is provided an apparatus for preparing an oligomer. The apparatus for preparing an oligomer can include a reactor 100 including a gaseous area 110 having a first gaseous reactant inlet 10 provided at a lower portion thereof; and a reaction area 120 in which a reaction medium RM reacts with the gaseous reactant above the gaseous area; a second gaseous reactant inlet 20 provided on an inner wall of the reactor 100 in the gaseous area 110 and a third gaseous reactant inlet 30 provided on an inner wall of the reactor 100 facing the second gaseous reactant inlet 20; and a first injection nozzle 22 connected to the second gaseous reactant inlet 20 and a second injection nozzle 32 connected to the third gaseous reactant inlet 30.

According to an exemplary embodiment of the present invention, the reactor 100 can prepare an oligomer product by performing an oligomerization reaction of a monomer in the presence of a catalyst and a solvent.

As a specific example, the gaseous reactant supplied to the gaseous area 110 can include the monomer, and the reaction medium RM included in the reaction area 120 can include the catalyst and the solvent. That is, the gaseous reactant including a gaseous monomer supplied to the gaseous area 110 can come into contact with the reaction area 120 including the liquid reaction medium RM containing the catalyst and the solvent to perform an oligomerization reaction, thereby producing an oligomer product.

According to an exemplary embodiment of the present invention, the reactor 100 can be a reactor 100 suitable for a continuous process. For example, the reactor 100 can be a bubble column reactor, which allows the preparation of an oligomer product continuously.

According to an exemplary embodiment of the present invention, the monomer can include an ethylene monomer. As a specific example, a gaseous reactant including the ethylene monomer can be supplied to the reactor 100 and subjected to the oligomerization reaction to prepare a desired α-olefin product.

In this case, the oligomerization reaction can be performed in an upper area of the gaseous area 110 in the reactor 100, and the oligomerization reaction of a monomer can be performed in a liquid reaction medium RM dissolved in a solvent, in the presence of a catalyst and a cocatalyst. As such, an area including the reaction medium RM in which the oligomerization reaction of a monomer is performed can be defined as the reaction area 120. The oligomerization reaction can refer to a reaction in which a monomer is oligomerized. The oligomerization reaction can be referred to as trimerization or tetramerization depending on the number of monomers to be polymerized, and these are collectively called multimerization.

The α-olefin is an important material which is used in comonomers, detergents, lubricants, plasticizers, etc., and is commercially widely used. Among them, 1-hexene and 1-octene have been widely used as comonomers for adjusting the density of polyethylene in the preparation of linear low density polyethylene (LLDPE). The α-olefin such as 1-hexene and 1-octene can be produced by, for example, a trimerization reaction or tetramerization reaction of ethylene.

The reaction medium RM can be supplied to the reaction area 120 through a reaction medium supply line L4. As a specific example, the reaction medium supply line L4 can be connected to the reaction area 120 through one side of the reactor 100.

The solvent can include, for example, one or more selected from the group consisting of n-pentane, n-hexane, n-heptane, cyclohexane, methylcyclohexane, octane, cyclooctane, decane, dodecane, benzene, xylene, 1,3,5-trimethylbenzene, toluene, ethylbenzene, chlorobenzene, dichlorobenzene, and trichlorobenzene.

The catalyst can include a transition metal source. The transition metal source can be, for example, a compound including one or more selected from the group consisting of chromium (III) acetylacetonate, chromium (III) chloride tetrahydrofuran, chromium (III) 2-ethylhexanoate, chromium (III) tris(2,2,6,6-tetramethyl-3,5-heptanedionate), chromium (III) benzoylacetonate, chromium (III) hexafluoro-2,4-pentanedionate, chromium (III) acetate hydroxide, chromium (III) acetate, chromium (III) butyrate, chromium (III) pentanoate, chromium (III) laurate, and chromium (III) stearate.

The cocatalyst can include, for example, one or more selected from the group consisting of trimethyl aluminium, triethyl aluminium, triisopropyl aluminium, triisobutyl aluminum, ethylaluminum sesquichloride, diethylaluminum chloride, ethyl aluminium dichloride, methylaluminoxane, modified methylaluminoxane, and borate.

As described above, as a type of a reactor in which the oligomerization reaction of ethylene is performed, a bubble column reactor for performing the oligomerization reaction (a trimerization reaction or a tetramerization reaction) of ethylene by bringing a gaseous ethylene monomer used as a reactant into contact with a reaction area 120 including a liquid reaction medium RM containing a catalyst can be used.

In the bubble column reactor, a gaseous reactant is introduced into and at the same time, dispersed in the reaction area 120 including the liquid reaction medium RM through a porous dispersion plate 130 provided between the gaseous area 110 and the reaction area 120 in the reactor 100, and turbulence is generated by a force of the dispersed gas, such that the liquid reaction medium and the gaseous reactant are naturally mixed with each other. In this case, a dispersing force of the gaseous reactant introduced into the reaction area 120 through the porous dispersion plate 130 is maintained to be greater than a head pressure acting downward from the liquid reaction medium RM, such that the liquid reaction medium RM can stay in the reaction area 120.

In addition, the most ideal position of the gaseous reactant inlet for efficient mixing of the gaseous reactant and the liquid reaction medium RM can be at the center of a lower portion of the reactor. However, in an initial stabilization stage in which the mixing is performed as described above, problems such as a hindrance of the dispersed flow of the gaseous reactant due to polymers (specifically, C10+ polymers), which are by-products generated during a catalytic reaction, other than a desired oligomer according to the reaction, or a momentary decrease in a supply flow rate of the gaseous reactant due to an operator's mistake in operating a flow rate control device may occur.

As a result, weeping, which is a phenomenon in which a part of the liquid reaction medium RM in the reaction area 120 is dropped into the gaseous area 110 at the lower portion of the reactor, may occur, and in this case, the liquid reaction medium RM falling into the gaseous area 110 may block the gaseous reactant inlet, thereby continuously obstructing the injection and flow of gas. Accordingly, a mixing efficiency in the reaction area 120 is significantly reduced, resulting in a problem of shutting down the operation of an entire process.

Thus, an object of the present invention is to provide an apparatus for preparing an oligomer according to the present invention, as a measure for ensuring a stable operation time without stopping a process operation by minimizing process instability in a short time when a weeping phenomenon occurs inside a reactor.

According to an exemplary embodiment of the present invention, the gaseous reactant can be supplied to the gaseous area 110 in the reactor 100 through the first gaseous reactant inlet 10 provided at a lower portion of the reactor 100. As a specific example, the gaseous reactant can be supplied from the outside of the reactor 100 through the first gaseous reactant supply line L1 connected to the first gaseous reactant inlet 10.

As described above, a gaseous reactant supplied to the gaseous area 110 is introduced into and, at the same time, dispersed in the reaction area 120 positioned above the gaseous area 110 and including the liquid reaction medium RM, through a porous dispersion plate 130 provided between the gaseous area 110 and the reaction area 120 in the reactor 100, and turbulence is generated by a force of the dispersed gas, such that the liquid reaction medium RM and the gaseous reactant are naturally mixed with each other.

The porous dispersion plate 130 includes a plurality of holes having a size large enough for the gaseous reactant to pass therethrough, and can serve to provide the gaseous reactant with a mobile power that can disperse the gaseous reactant into the reaction area 120 while the gaseous reactant passes through the holes. As a specific example, as the gaseous reactant passes through the porous dispersion plate 130 and is introduced into the reaction area 120, a force for the gaseous reactant to rise and a force pressed by the liquid reaction medium RM are generated in combination. Accordingly, turbulence is generated by an upward flow and a downward flow, such that the gaseous reactant can be dispersed and the gaseous reactant can be mixed with the liquid reaction medium RM.

In the reaction area 120, an oligomerization reaction is performed by a catalytic reaction of the gaseous reactant in a process of mixing the reaction medium RM and the gaseous reactant with each other. The oligomer product prepared by the oligomerization reaction is in a liquid state, and can be discharged through a product discharge line L5 provided on the other side of the reactor 100, that is, the other side facing the one side having the reaction medium supply line L4 in reactor 100 described above.

Since the product discharge stream discharged through the product discharge line L5 can include an oligomeric product and a solvent, the oligomer product and the solvent can be separated through an additional separation device (not illustrated), and the separated solvent can be reused in the reaction area 120. When an ethylene monomer is included as the gaseous reactant, the oligomer product, for example, can include 1-hexene and 1-octene.

Meanwhile, the unreacted materials that have not been oligomerized in the reaction area 120 are unreacted vapors in a gaseous state, and can be discharged upward of the reactor 100 through an unreacted vapor discharge line L6 provided at the top of the reactor 100.

The most ideal position of the gaseous reactant inlet for efficient mixing of the reaction medium RM and the dispersed gaseous reactant in the reaction area 120 is at the center of a lower portion of the reactor. Accordingly, a conventional bubble column reactor has the first gaseous reactant inlet 10 in the central position of the bottom of the reactor 100.

However, in this case, as described above, when the liquid reaction medium RM dropped to the gaseous area 110 due to the weeping phenomenon blocks the first gaseous reactant inlet 10, the mixing efficiency in the reaction area 120 is significantly reduced, resulting in a problem of shutting down the operation of an entire process.

In order to solve this problem, the apparatus for preparing an oligomer according to the present invention includes a second gaseous reactant inlet 20 provided on an inner wall of the reactor 100 in the gaseous area 110 and a third gaseous reactant inlet 30 provided on an inner wall of the reactor 100 facing the second gaseous reactant inlet 20, such that when the liquid reaction medium RM blocks the first gaseous reactant inlet 10 due to the weeping phenomenon during the reaction, a gaseous reactant can be supplied to a gaseous area 110 through the second gaseous reactant inlet 20 and the third gaseous reactant inlet 30.

As a specific example, the gaseous reactant can be supplied from the outside of the reactor 100 through a second gaseous reactant supply line L2 connected to the second gaseous reactant inlet 20 and a third gaseous reactant supply line L3 connected to the third gaseous reactant inlet 30.

As a specific example, the gaseous reactant can be supplied from the outside of the reactor 100 through a second gaseous reactant supply line L2 branched from the first gaseous reactant supply line L1 and connected to the second gaseous reactant inlet 20 and a third gaseous reactant supply line L3 branched from the first gaseous reactant supply line L1 and connected to the third gaseous reactant inlet 30.

According to an exemplary embodiment of the present invention, the apparatus for preparing an oligomer according to the present invention can further include first, second, and third flow rate control devices V1, V2, and V3 provided in the first, second, and third gaseous reactant supply lines L1, L2, and L3, respectively.

As such, the first, second, and third flow rate control devices V1, V2, and V3 respectively provided in the first, second, and third gaseous reactant supply lines L1, L2, and L3 can serve to control the flow rate of the gaseous reactant supplied to each gaseous reactant supply line. As a specific example, the first, second, and third flow rate control devices V1, V2, and V3 can be valves or pumps, but are not limited thereto, and more specifically, can be valves.

For example, if the weeping phenomenon described above makes it difficult to supply the gaseous reactant through the first gaseous reactant inlet 10, the first flow rate control device V1 provided in the first gaseous reactant supply line L1 is closed to block the gaseous reactant stream introduced into the first gaseous reactant inlet 10, and then the closed second and third flow rate control devices are opened to supply a gaseous reactant to the gaseous area 110 through the second and third gaseous reactant supply lines L2 and L3. Accordingly, it is possible to ensure a stable operation time without stopping the process by minimizing process instability in a short time due to the occurrence of a weeping phenomenon.

According to an exemplary embodiment of the present invention, the apparatus for preparing an oligomer according to the present invention can include a first injection nozzle 22 connected to the second gaseous reactant inlet 20 and a second injection nozzle 32 connected to the third gaseous reactant inlet 30. That is, the apparatus for preparing an oligomer can include injection nozzles 22 and 32 for injecting the gaseous reactant supplied through the second and third gaseous reactant inlets 20 and 30 into the gaseous area 110.

As a specific example, the first and second injection nozzles 22 and 32 are the gaseous area 110 in the reactor 100, and can be connected to the second and third gaseous reactant inlets 20 and 30, respectively. In this case, the second and third gaseous reactant inlets 20 and 30 can be positioned on the same horizontal line, and accordingly, the first and second injection nozzles 22 and 32 can also be located on the same horizontal line. That is, the first and second injection nozzles 22 and 32 can be provided at the same height inside the reactor 100.

The apparatus for preparing an oligomer can further include a first nozzle pipe 24 for connecting the first injection nozzle from the second gaseous reactant inlet 20, or a second nozzle pipe 34 for connecting the second injection nozzle 32 from the third gaseous reactant inlet 30. As a specific example, the shape of the first nozzle pipe 24 and the second nozzle pipe 34 can be straight, but is not limited thereto.

Each of the first and second injection nozzles 22 and 32 can include at least one injection port. In addition, each of the first and second injection nozzles 22 and 32 can be implemented in the form of a spray including a plurality of injection ports. For example, the first and second injection nozzles 22 and 32 can have one to five, one to four, or two to four injection ports. As a specific example, as illustrated in FIG. 1, the first and second injection nozzles 22 and 32 can be implemented in a form including three injection ports, respectively.

The injection pressure of the gaseous reactant injected through the first and second injection nozzles 22 and 32 can be 0.1 to 0.3 Mpa higher than the pressure acting downward from the liquid reaction medium RM. At a pressure within the above range, the gaseous reactant can be injected through the first and second injection nozzles 22 and 32 to be uniformly dispersed in the gaseous area 110. As such, when the uniformly dispersed gaseous reactant is introduced into the reaction area 120 through the porous dispersion plate 130, mixing with the liquid reaction medium RM can be performed uniformly, thereby improving a mixing efficiency in the reaction area 120.

According to an exemplary embodiment of the present invention, the apparatus for preparing an oligomer according to the present invention can further include a first deflector 26 and a second deflector 36 each provided on the inner wall of the reactor 100 above the second gaseous reactant inlet 20 and the third gaseous reactant inlet 30. The first and second deflectors 26 and 36 can serve to change the flow of the gaseous reactant that is injected from the first and second injection nozzles 22 and 32 through the second gaseous reactant inlet 20 and the third gaseous reactant inlet 30 and flows upward in the opposite direction.

As a specific example, the first and second deflectors 26 and 36 are provided on the inner wall of the reactor 100 in an area between the first and second injection nozzles 22 and 32 and the porous dispersion plate 130. The gaseous reactant injected from the first injection nozzle 22 and the second injection nozzle 32 provided on the inner wall of the reactor 100 of the gaseous area 110 can have a flow biased toward a hole adjacent to the inner wall of the reactor 100 among the holes of the porous dispersion plate 130. As described above, when the first and second deflectors 26 and 36 are included, such a biased flow is prevented, and a uniform flow of the gaseous reactant can be induced into all holes of the porous dispersion plate 130.

According to an exemplary embodiment of the present invention, an injection angle of the gaseous reactant injected from the first injection nozzle 22 and the second injection nozzle 32 can be 40 to 50° in a downward direction of the reactor 100. In this case, the injection angle can be an angle of a first nozzle pipe connecting the first injection nozzle from the second gaseous reactant inlet 20, or a second nozzle pipe connecting the second injection nozzle 32 from the third gaseous reactant inlet 30.

As a specific example, the injection angle of the gaseous reactant injected from the first injection nozzle 22 and the second injection nozzle 32 can be 40 to 50°, 42 to 48°, or 44 to 46° in a downward direction of the reactor 100. In this case, a phenomenon in which the introduction of the gaseous reactant is biased into the hole of the porous dispersion plate 130 positioned in an inner wall direction of the reactor 100 can be minimized, such that the mixing efficiency of the reaction medium RM and the gaseous reactant in the reaction area 120 can be improved, thereby improving the oligomerization reaction efficiency.

According to an exemplary embodiment of the present invention, a height of the gaseous area 110 can be 70 to 90%, 70 to 85%, or 75 to 80% relative to the diameter of the reactor 100. In this case, the gaseous area 110 in the reactor 100 can serve as a sufficient buffer, so that even when an unstable downward drift of the liquid reaction medium RM occurs, the occurrence of a weeping phenomenon in the gaseous area 110 positioned at a lower portion can be minimized. Thus, it is possible to perform stable operation even if the gaseous reactant is not injected through the first gaseous reactant inlet 10 positioned at the exact center of the gaseous area 110.

According to an exemplary embodiment of the present invention, there is provided a method for preparing an oligomer using the apparatus for preparing an oligomer according to the present invention.

The method for preparing an oligomer using the apparatus for preparing an oligomer according to the present invention can include supplying a gaseous reactant to the gaseous area through the second and third gaseous reactant supply lines by closing the first flow rate control device and opening second and third flow rate control devices when the first gaseous reactant inlet is blocked.

As described above, for example, if the weeping phenomenon described above blocks the first gaseous reactant inlet 10, making it difficult to supply the gaseous reactant through the first gaseous reactant inlet 10, the first flow rate control device V1 provided in the first gaseous reactant supply line L1 is closed to block the gaseous reactant stream introduced into the first gaseous reactant inlet 10, and then the closed second and third flow rate control devices are opened to supply a gaseous reactant to the gaseous area 110 through the second and third gaseous reactant supply lines L2 and L3. Accordingly, it is possible to ensure a stable operation time without stopping the process by minimizing process instability in a short time due to the occurrence of a weeping phenomenon.

As a specific example, when the temperature of the gaseous area 110 rapidly rises, it can be determined that the liquid reaction medium RM is introduced into the gaseous area 110 and the first gaseous reactant inlet 10 is blocked, and thus, it is possible to close the first flow rate control device V1 and open the second and third flow rate control devices V2 and V3.

According to an exemplary embodiment of the present invention, when the first flow rate control device V1 is closed to block the gaseous reactant stream introduced into the first gaseous reactant inlet 10, each of ratios of flow rates of the gaseous reactants supplied to the gaseous area 110 through the second gaseous reactant supply line L2 and the third gaseous reactant supply line L3 can be 40 to 60%, 45 to 55%, or 48 to 52%, with respect to the total flow rate of the gaseous reactant supplied to the first gaseous reactant supply line L1.

As a specific example, the flow rate of the gaseous reactant supplied to the gaseous area 110 through the second gaseous reactant supply line L2 can be 40 to 60%, 45 to 55%, or 48 to 52%, with respect to the total flow rate of the gaseous reactant supplied to the first gaseous reactant supply line L1, and the flow rate of the gaseous reactant supplied to the gaseous area 110 through the third gaseous reactant supply line L3 can be 40 to 60%, 45 to 55%, or 48 to 52%, with respect to the total flow rate of the gaseous reactant supplied to the first gaseous reactant supply line L1. Within the above range, the uniform dispersion effect of the gaseous reactant through the porous dispersion plate 130 can improve the mixing efficiency of the reaction medium RM and the gaseous reactant in the reaction area 120.

For example, as described above, adjusting each of ratios of flow rates of the gaseous reactants supplied to the gaseous area 110 through the second gaseous reactant supply line L2 and the third gaseous reactant supply line L3, can be performed by controlling the second flow rate control device V2 and the third flow rate control device V3.

According to an exemplary embodiment of the present invention, the apparatus for preparing an oligomer can further install an apparatus necessary for preparing an oligomer, such as a flow control device (not illustrated), a condenser (not illustrated), a reboiler (not illustrated), a pump (not illustrated), a cooling facility not illustrated), a filter (not illustrated), a stirrer (not illustrated), a separation device (not illustrated) a compressor (not illustrated), and a mixer (not illustrated), if necessary.

The apparatus for preparing an oligomer according to the present invention has been described and has been shown in the drawings herein, but only essential configurations for understanding the present invention have been described and have been illustrated in the drawings, and processes and apparatuses that are not separately described and illustrated, in addition to processes and apparatus described above and illustrated in the drawings, may be appropriately applied and used in order to implement the apparatus for preparing an oligomer according to the present invention.

The invention claimed is:

1. An apparatus for preparing an oligomer, comprising:
   a reactor including a gaseous area having a first gaseous reactant inlet provided at a lower portion thereof, and a reaction area in which a reaction medium contacts with a gaseous reactant above the gaseous area;
   a second gaseous reactant inlet provided on an inner wall of the reactor in the gaseous area and a third gaseous reactant inlet provided on an inner wall of the reactor facing the second gaseous reactant inlet;
   a first injection nozzle connected to the second gaseous reactant inlet and a second injection nozzle connected to the third gaseous reactant inlet, and
   a porous dispersion plate provided between the gaseous area and the reaction area.

2. The apparatus for preparing an oligomer of claim 1, further comprising:
   a first gaseous reactant supply line connected to the first gaseous reactant inlet;
   a second gaseous reactant supply line branched from the first gaseous reactant supply line and connected to the second gaseous reactant inlet and a third gaseous reactant supply line branched from the first gaseous reactant supply line and connected to the third gaseous reactant inlet; and
   first, second, and third flow rate control devices provided in the first, second, and third gaseous reactant supply lines, respectively.

3. The apparatus for preparing an oligomer of claim 1, wherein the reaction medium is in a liquid state.

4. The apparatus for preparing an oligomer of claim 1, wherein the first gaseous reactant inlet is positioned in the center of a lower part of the reactor.

5. The apparatus for preparing an oligomer of claim 1, further comprising a first deflector and a second deflector each provided on the inner wall of the reactor above the second gaseous reactant inlet and the third gaseous reactant inlet, respectively.

6. The apparatus for preparing an oligomer of claim 1, wherein an injection angle of the gaseous reactant injected from the first injection nozzle and the second injection nozzle is 40 to 50° in a downward direction of the reactor.

7. The apparatus for preparing an oligomer of claim 1, wherein a height of the gaseous area is 70 to 90% relative to a diameter of the reactor.

8. The apparatus for preparing an oligomer of claim 1, further comprising:
   a reaction medium supply line for supplying the reaction medium to the reaction area;
   a product discharge line for discharging a product from the reaction area; and
   an unreacted vapor discharge line for discharging unreacted vapors from the reactor.

9. The apparatus for preparing an oligomer of claim 1, wherein the gaseous reactant includes ethylene, and the oligomer includes an α-olefin.

10. A method for preparing an oligomer using the apparatus of claim 2, the method comprising:
    supplying a gaseous reactant to the gaseous area through the second and third gaseous reactant supply lines by closing the first flow rate control device and opening second and third flow rate control devices when the first gaseous reactant inlet is blocked.

11. The method of claim 10, wherein each of ratios of flow rates of the gaseous reactants supplied to the gaseous area through the second gaseous reactant supply line and the third gaseous reactant supply line is 40 to 60% with respect to the total flow rate of the gaseous reactant supplied to the first gaseous reactant supply line.

* * * * *